(12) United States Patent
Plassky et al.

(10) Patent No.: US 10,335,239 B2
(45) Date of Patent: Jul. 2, 2019

(54) DISPOSABLE REFLECTIVE MARKER

(71) Applicant: Brainlab AG, Munich (DE)

(72) Inventors: Norman Plassky, Erfurt (DE); Hansjoerg Huber, Wasserburg (DE)

(73) Assignee: Brainlab AG, Munich (DE)

( * ) Notice: Subject to any disclaimer, the term of this patent is extended or adjusted under 35 U.S.C. 154(b) by 915 days.

(21) Appl. No.: 14/760,747

(22) PCT Filed: Feb. 20, 2013

(86) PCT No.: PCT/EP2013/053349
§ 371 (c)(1),
(2) Date: Jul. 14, 2015

(87) PCT Pub. No.: WO2014/127814
PCT Pub. Date: Aug. 28, 2014

(65) Prior Publication Data
US 2015/0351863 A1  Dec. 10, 2015

(51) Int. Cl.
*A61B 5/05* (2006.01)
*A61B 34/20* (2016.01)
*A61B 90/00* (2016.01)
*A61B 17/00* (2006.01)

(52) U.S. Cl.
CPC ............... *A61B 34/20* (2016.02); *A61B 90/39* (2016.02); *A61B 2017/0023* (2013.01); *A61B 2017/00477* (2013.01); *A61B 2034/2055* (2016.02); *A61B 2090/397* (2016.02); *A61B 2090/3937* (2016.02); *A61B 2090/3983* (2016.02); *A61B 2090/3991* (2016.02)

(58) Field of Classification Search
None
See application file for complete search history.

(56) References Cited

U.S. PATENT DOCUMENTS

| | | | | |
|---|---|---|---|---|
| 2003/0225329 A1* | 12/2003 | Rossner | ................. | A61B 90/39 600/424 |
| 2004/0030236 A1* | 2/2004 | Mazzocchi | ............ | A61B 90/39 600/414 |
| 2009/0183740 A1* | 7/2009 | Sheffer | ................. | A61B 90/39 128/882 |

FOREIGN PATENT DOCUMENTS

| | | |
|---|---|---|
| DE | 20 2004 011567 | 11/2004 |
| DE | 10 2007 055 456 | 5/2009 |
| WO | 2007/136784 | 11/2007 |

OTHER PUBLICATIONS

International Search Report and Written Opinion for International Application No. PCT/EP2013/053349 dated Nov. 20, 2013 (3 pages).

* cited by examiner

*Primary Examiner* — Joel F Brutus
(74) *Attorney, Agent, or Firm* — Tucker Ellis LLP

(57) ABSTRACT

The present invention relates to a marker for optical medical navigation, comprising a structure (1) with at least one recess (3), and at least one supporting element (2), wherein each supporting element (2) is configured to be accommodated within a particular recess (3) and to support at least one optically detectable element (4), and wherein each recess (3) has a first opening (5) which allows a supporting element (2) to be introduced into the recess (3), wherein the recess (3) has at least two second openings (6) which are different from the first opening (5), wherein each of the at least two second openings (6) is configured to allow the at least one optically detectable element (4) supported by the supporting element (2) to be optically detected.

19 Claims, 4 Drawing Sheets

DISPOSABLE REFLECTIVE MARKER

RELATED APPLICATION DATA

This application is a national phase application of International Application No. PCT/EP2013/053349 filed Feb. 20, 2013 and published in the English language.

The present invention relates to a medical tracking marker which is used when an object is to be localised or tracked by means of an optical medical tracking system.

Medical tracking markers are known in general, for example from DE 196 39 615 A1, and are used in conjunction with a medical navigation system. The above-referenced document discloses spherical markers which are to be fixed on the patient or on medical instruments via a suitable structure or "post". The markers can be screwed onto this structure so as to be held in a predetermined position relative to each other. However, producing such spherical markers as a disposable product is cost-intensive, and it is time-consuming to attach such markers to a structure, for example by screwing the individual markers onto a respective structure.

It is an object of the present invention to overcome at least one of the problems described above and in particular to provide a marker or marker array which is inexpensive to produce and which can be quickly and simply assembled to form a marker array exhibiting a predetermined geometry.

The marker in accordance with the invention comprises a structure with at least one recess, and at least one supporting element, wherein each supporting element is configured to be accommodated within a particular recess and to support at least one optically detectable element, and wherein each recess has a first opening, which allows a supporting element to be introduced into the recess, and at least two second openings which are different from the first opening, wherein each of the at least two second openings is configured to allow the at least optically detectable element supported by the supporting element to be optically detected.

In other words, the marker in accordance with the invention comprises a structure which encompasses at least one supporting element, wherein at least one optically detectable element is held in place by the structure and a supporting element, such that the optically detectable element can be "seen" by an optical medical tracking system through at least two second openings formed in the structure or "body" of the marker. The structure itself can comprise any means suitable for attaching the structure to an object to be tracked by a medical tracking system. Moreover, the at least one supporting element can be inserted together with at least one optically detectable element into particular recesses of the structure such that the at least one optically detectable element is positionally fixed to the object to be tracked and, if a plurality of optically detectable elements are used, positionally fixed relative to other optically detectable elements by means of supporting elements and the structure of the marker.

In order to assemble a marker for use with an optical medical tracking system, it is merely necessary to provide one or more optically detectable elements, place it/them onto one or more supporting elements and insert the one or more supporting elements together with the optically detectable elements into the marker structure, without any tedious assembly procedures.

In accordance with a further embodiment of the present invention, the optically detectable element is a reflective layer, in particular a layer of reflective fabric. For modern optical tracking systems, tracking markers are used which comprise a light-reflective surface, such that electromagnetic radiation such as visible or infrared light directed at the markers is reflected towards a camera array of an optical medical tracking system. In accordance with the present invention, the structure and the supporting elements can be configured to retain a two-dimensional reflective layer. It is also preferred if the marker in accordance with the invention is configured to retain a reflective fabric layer, which is already known in conjunction with spherical tracking markers.

In accordance with another embodiment of the present invention, the second openings have a predetermined contour, in particular a circular contour, wherein the structure and at least one of the supporting elements are specifically configured to retain at least one optically detectable element in such a way that the contour of a detectable part of the at least one optically detectable element supported by the supporting element corresponds to the contour of the second openings. It could also be said that the structure and at least one of the supporting elements allow only certain parts of an optically detectable element to be optically detected. These certain parts can be defined by the contour of the openings in the marker structure, wherein this contour has to be suitable for use in conjunction with an optical tracking system. For example, the contour of at least one opening can be a circular contour, since the centre of a "circular" marker can be easily determined from various directions by an optical tracking system.

It is also possible for the structure of the marker and/or at least one of the at least one supporting elements to be configured to retain an optically detectable element which extends beyond the contour of at least one of the second openings assigned to said optically detectable element. The supporting elements and the structure can for example "pinch" the optically detectable elements in a frictional fit and/or positive fit in a region which extends beyond the contour of at least one of the second openings.

A plurality of the second openings of the marker in accordance with the invention can also be configured to allow at least one optically detectable element supported by the supporting elements to be optically detected from substantially the same direction. The openings are then "directed" towards essentially the same direction, such that a camera array can see several optically detectable elements through a plurality of openings of the same marker.

It is also possible for a plurality of the second openings to be configured to allow at least one optically detectable element supported by the supporting element to be optically detected from different directions, in particular from opposite directions, wherein the second openings are specifically situated in respective pairs which are exactly opposite each other.

In accordance with another embodiment of the present invention, at least one of the supporting elements extends over a plurality of the second openings, such that the same optically detectable element can be seen through a plurality of second openings. Consequently, it is possible to fill a plurality of openings with a small number of optically detectable elements, thus further reducing the effort involved in assembling the marker.

It is also possible for at least one of the second openings to have a chamfered edge facing away from the recess. Such a chamfered edge can exhibit any shape which is suitable for increasing the visibility of the optically detectable element situated within the opening, such that the visibility of the optically detectable element is ensured over a wide range. The second openings can be machined into the marker structure so as to achieve narrow tolerances with respect to the contour of the optically detectable elements, whether or not the second opening(s) has/have a chamfered edge.

It is also conceivable for at least one of the supporting elements to provide at least one supporting surface, in particular a flat surface, for at least one of the optically detectable elements, and in particular two supporting surfaces which face away from each other. Although a supporting element could provide a frame for one or more optically detectable elements, the supporting elements preferably support at least one optically detectable element by way of a rigid supporting surface which contacts the optically detectable element. In this way, it is also possible to shape a non-rigid optically detectable element by means of a supporting surface having a predetermined shape.

Furthermore, a supporting element having two supporting surfaces facing away from each other is conceivable in connection with second openings which are formed in the marker structure and situated in paws exactly opposite each other, so as to allow the marker to be detected from opposite directions.

In accordance with another embodiment of the present invention, at least one of the supporting elements comprises at least one cavity which is configured to accommodate an optically detectable element, wherein said at least one of the supporting surfaces is in particular formed by at least one of the cavities. This can help to prevent damage to the optically detectable element as it is introduced together with the supporting element into the recess of the marker structure.

The depth of at least one of the cavities can essentially correspond to the thickness of an optically detectable element situated within the cavity. The marker structure and the supporting element are then still able to pinch the optically detectable element after it has been introduced into the marker structure.

It is conceivable for the marker structure and/or at least one of the supporting elements to have a resilient configuration in order to provide a detachable positive fit and/or frictional fit between the structure and at least one of the supporting elements and/or retain an optically detectable element supported by a supporting element. Forces generated by elastically deforming the structure and/or a supporting element can be used to retain the optically detectable element and hold the supporting element within the recess of the marker structure while the marker is being used for navigation.

The structure of the marker and/or at least one of the supporting elements can also comprise a release section which is resiliently hinged to the structure and/or supporting element(s) and configured to release the positive fit or frictional fit formed between the structure and the supporting element(s), in particular by being elastically deformed, specifically compressed or pulled apart. The user can for example move ends of resiliently hinged arms towards or away from each other for this purpose.

Once the marker has been used for navigation purposes, a user can easily remove the supporting elements together with the optically detectable elements from the marker structure. The supporting elements may be snap-fitted to the marker structure.

In general, the marker structure and the supporting elements can be separated from each other after use in order to allow one or more elements of the marker to be discarded. This allows the supporting elements to be formed from plastics, as cheap and easily disposable elements of the marker in accordance with the invention. It is also conceivable for the marker structure to be formed from a higher-quality material, for example metal, in order to allow it to be used repeatedly.

In accordance with another embodiment of the present invention, at least one of the supporting elements comprises a gripping section which protrudes from the first opening and which can also form the release section. Once the marker has been used, a user can disassemble the marker by using the gripping section to draw the supporting elements, together with the optically detectable element, out of the marker structure, wherein it is conceivable that the gripping section is also used as the release section for releasing a frictional fit or positive fit between the marker structure and a supporting element.

In accordance with another embodiment of the present invention, the position of a plurality of the second openings with respect to each other conforms to a predetermined marker arrangement which is recognised by an optical medical tracking system.

In the following, embodiments of the invention will be described in more detail by referring to the attached drawings. It should be noted that each of the features of the present invention as referred to herein can be implemented separately or in any expedient combination.

Figure 1:
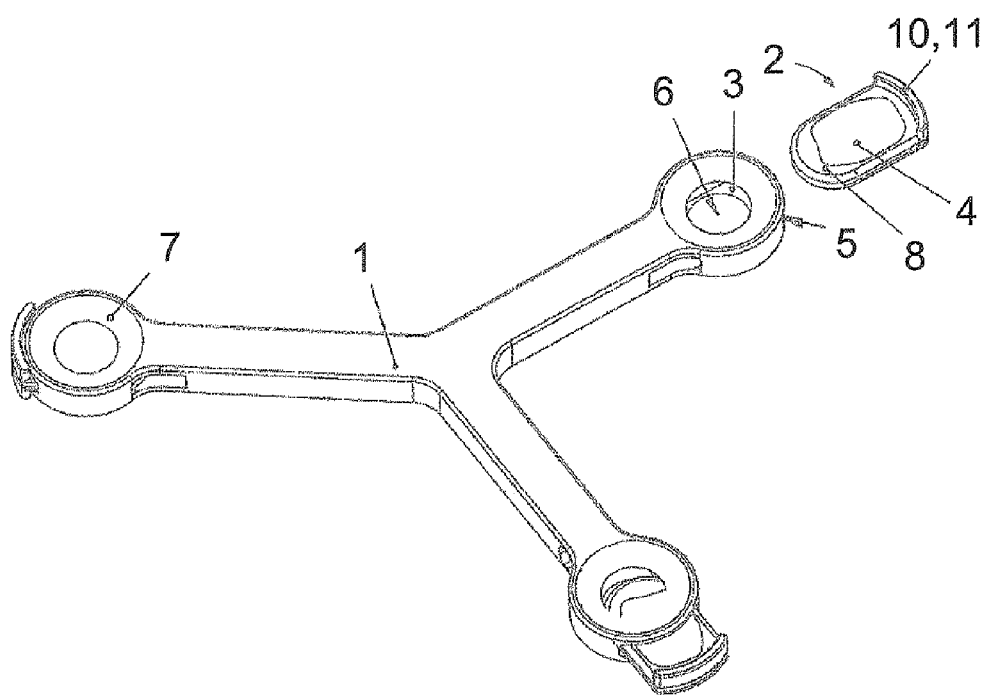
FIG. 1 shows a first embodiment of the marker in accordance with the invention.

FIG. 1 shows a first embodiment of a marker in accordance with the invention, comprising a structure 1 and three supporting elements 2. The star-shaped structure 1 has a recess 3 for each supporting element 2 at the end of each of its three arms. Each recess 3 comprises a first opening 5, which allows a supporting element 2 to be inserted, and two circular second openings 6 which are situated exactly opposite each other.

To assemble the marker in accordance with the invention, the user places a reflective fabric layer 4 onto the two mutually opposite supporting surfaces 8 of the supporting element 2. Only one supporting surface 8 can be seen in FIG. 1, while the second surface 8, which is flat, is situated on the lower side of the supporting element 2 and extends parallel to the first surface 8, which is also flat. Instead of simply being placed onto the supporting surfaces 8 of the supporting element 2, the reflective layers can also be attached, for example glued, to the supporting surfaces 8, thereby providing a pre-assembled supporting element as a sterile disposable.

Each of the supporting elements 2 can then be inserted into a particular recess 3 of the structure 1 as shown in FIG. 1, in a clockwise direction starting from the upper right corner in FIG. 1. As can also be seen in FIG. 1, each supporting element 2 comprises a gripping section 11 which allows a user to press one end of the supporting element 2 together. This reduces the thickness of the supporting element 2, such that the supporting element 2 can be introduced into a particular recess 3 of the structure 1. Once the supporting element 2 has reached its final position within a recess 3, the gripping section 11 is released and the supporting element 2 is then held in the recess 3 by a frictional fit between the structure 1 and the supporting element 2. The resilient configuration of the supporting element 2 means that a spring force is applied, thus generating a frictional fit. This spring force also causes the reflective fabric layer 4 to be "pinched" between the structure 1 and the supporting element 2.

Each second opening 6 is precisely machined into the re-usable structure 1 together with a chamfered edge 7 which allows the reflective fabric layers 4 a wide range of visibility within the respective second openings 6. Once the marker has been used, it can be disassembled in the reverse order. A user can grip the gripping section 11 formed at the end of each supporting element 2 and push the two parts of the gripping section 11 together. The gripping section 11 therefore also serves as a releasing section 10. Instead of a frictional fit, a releasable positive fit can also be provided in this embodiment.

The respective supporting element 2 can then be drawn out of each of the recesses 3, together with the reflective fabric layers 4. Damaged and/or contaminated reflective fabric layers 4 can be discarded together with the supporting elements 2, while the structure 1 can be sterilised for subsequent use or can also be discarded. It is also possible to provide the supporting elements as re-usables which can be sterilized.

It can also be seen from FIG. 1 that the contour of the reflective fabric layers 4 can be fairly coarse, i.e. uneven, as long as it extends beyond the contour of a respective second opening 6. Ultimately, the second openings 6 determine the effective contour of each reflective fabric layer 4.

Figure 2:
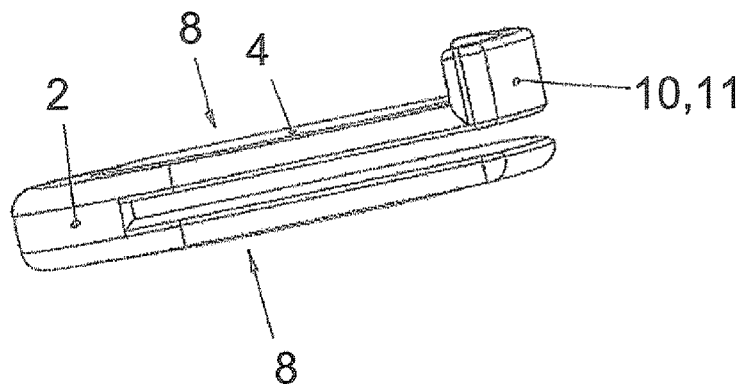
FIG. 2 shows a first embodiment of a supporting element.

FIG. 2 shows a preferred embodiment of a supporting element 2 comprising two parallel flat supporting surfaces 8 facing away from each other, to which reflective fabric layers 4 can be attached. It can be seen in FIG. 2 that the supporting element 2 has a resilient configuration comprising a hinge at a first end of the supporting element 2 (on the left-hand side in FIG. 2) and a gripping and releasing section 10, 11 at a second end of the supporting element 2 which is configured to be pushed together via the hinged arms of the supporting element 2 which are formed by the supporting surfaces 8. In this example, the gripping section 11 is also the releasing section 10 which is configured to release the frictional fit which holds the supporting element 2 in place within a particular recess 3 of the structure 1.

Figure 3:
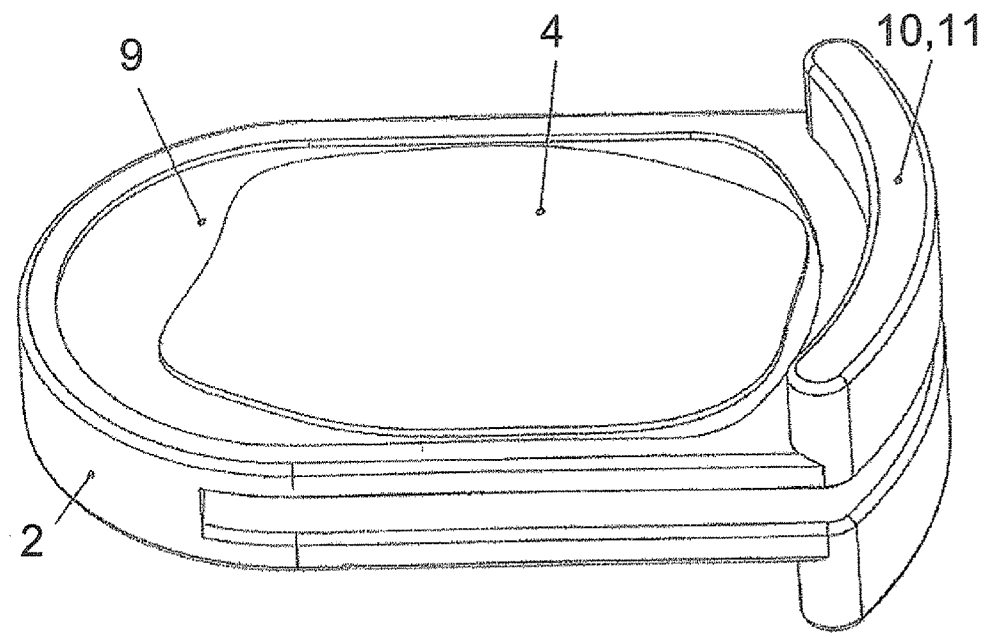
FIG. 3 shows a second embodiment of a supporting element, comprising a recess for an optically detectable element.

FIG. 3 shows a second embodiment which differs from the embodiment shown in FIG. 2 primarily in that a cavity 9 is formed on the upper surface 8 of the supporting element 2. A second cavity 9 (not visible in FIG. 3) is formed on the lower surface 8.

The cavity 9 accommodates a reflective fabric layer 4 which is therefore secure against being damaged when the supporting element 2 is introduced into a recess 3 of the structure 1.

Figure 4:
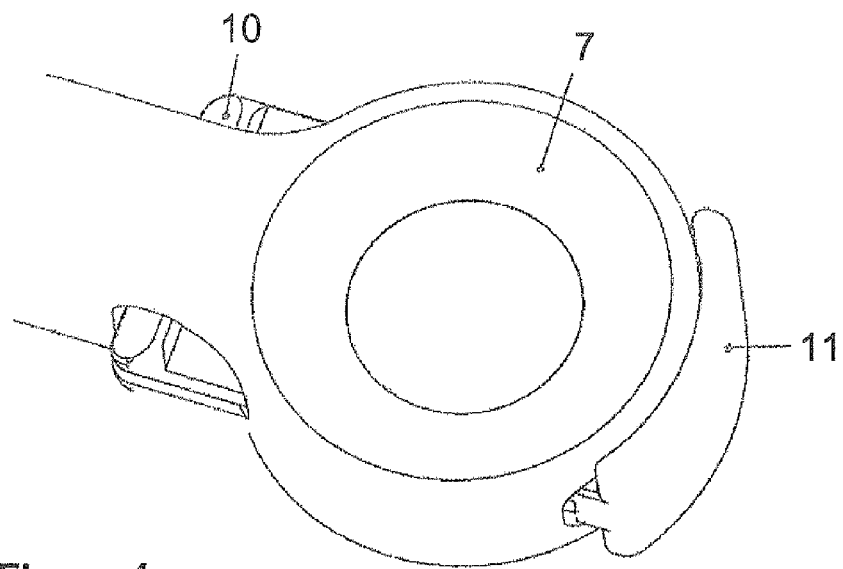
FIG. 4 shows a third embodiment of a supporting element.
Figure 5:
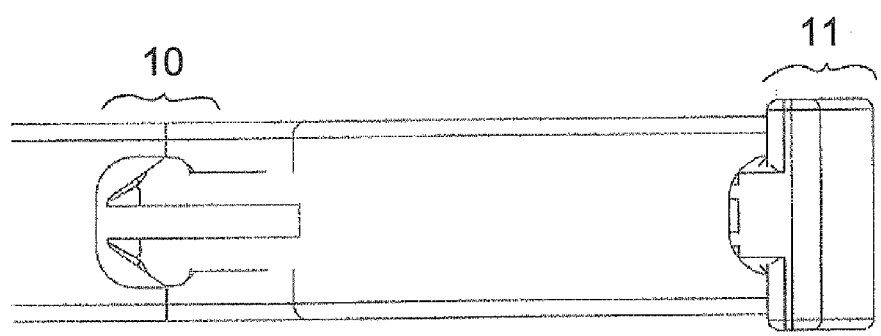
FIG. 5 shows a side view of the supporting element shown in FIG. 4.

FIGS. 4 and 5 show a second embodiment of a supporting element 2, in which the releasing section 10 is different from the gripping section 11, the releasing section 10 and the gripping section 11 being situated at opposite ends of the supporting element 2. As also shown in the foregoing embodiment, the gripping section 11 protrudes from the recess 3, such that a user is able to grip the gripping section 11 from without. The releasing section 10 protrudes from separate openings and forms a snap-fit to hold the supporting element 2 in place. The shape of the releasing section however hinders but does not block movement of the supporting element 2 completely so as to allow for removing the supporting element 2 from the marker structure 1.

Figure 6:
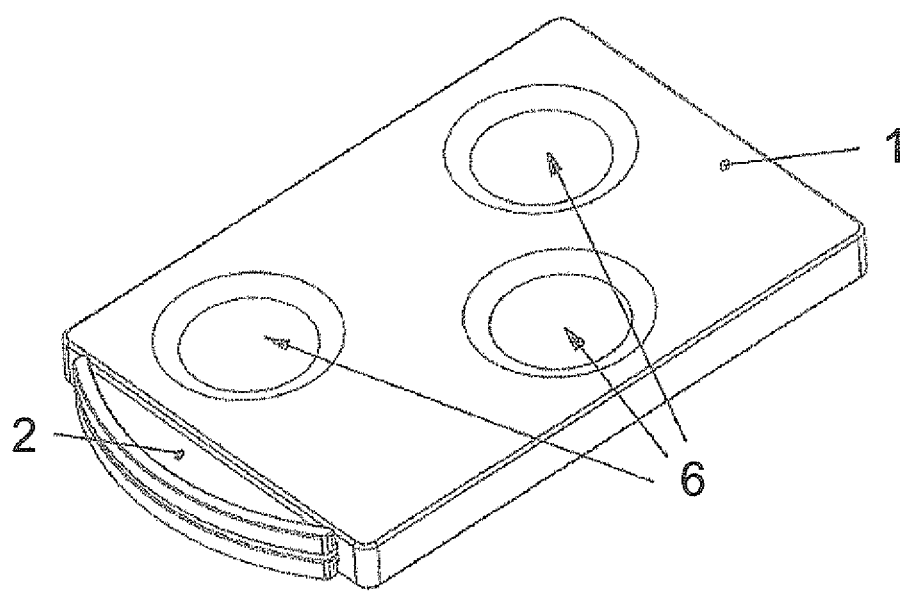
FIG. 6 shows a second embodiment of the marker in accordance with the invention.

FIG. 6 shows a second embodiment of the marker structure 1 in accordance with the invention, in which several openings 6 are formed on the same side of the structure 1, thereby allowing the reflective fabric layer 4 within them to be detected from the same direction. It is also possible for the structure 1 shown in FIG. 6 to additionally comprise corresponding openings 6 on its lower side, as already shown in the foregoing embodiments of the present invention. The supporting element 2 is configured to extend across all the openings 6 formed on one side of the structure 1, wherein a separate reflective fabric layer 4 can be provided for each opening 6 or one or more reflective fabric layers 4 can be provided for a plurality of openings 6.

The invention claimed is:

1. A marker for optical medical navigation, the marker comprising a structure with one or more recesses, and one or more supporting elements, wherein the one or more supporting elements are accommodated within the one or more recesses and support one or more optically detectable elements wherein the one or more recesses have a first opening which allows the one or more optically detectable elements together with one of the one or more supporting elements to be introduced into one of the one or mote recesses, and wherein:

the one or more recesses each have at least two second openings which are different from the first opening, wherein each of the at least two second openings has a predetermined contour and allows one of the one or more optically detectable elements to be optically detected therethrough, wherein the structure and the one or more supporting elements retain the at least one of the one or more optically detectable element within one of the one or more recess, and wherein a detectable shape of the one or more optically detectable elements is confined by the predetermined contours of the at least two second openings.

2. The marker according to claim 1, wherein at least one of the one or more optically detectable element is a reflective layer.

3. The marker according to claim 1, wherein the at least two second openings have a circular contour.

4. The marker according to claim 3, wherein the structure and/or at least one of the one or more supporting elements retain an optically detectable element which extends beyond the predetermined contour of at least one of the at least two second openings assigned to the one or more optically detectable elements.

5. The marker according to claim 1, wherein a plurality of the at least two second openings allow at least one optically detectable element supported by one of the one or more supporting elements to be optically detected from the same direction.

6. The marker according to claim 5, wherein at least one of the one or more supporting elements extends over a plurality of the at least two second openings.

7. The marker according to claim 1, wherein a plurality of the at least two second openings allow at least one optically detectable element supported by one or the one or more supporting elements to be optically detected from different directions.

8. The marker according to claim 1, wherein at least one of the at least two second openings has a chamfered edge facing away from the at least one recess.

9. The marker according to claim 1, wherein at least one of the one or more supporting elements provides at least one supporting surface, for at least one of the one of more optically detectable elements.

10. The marker according to claim 1, wherein at least one of the one or more supporting elements comprises at least one cavity which accommodates an optically detectable element, wherein at least one of the supporting surfaces is formed by the at least one cavity.

11. The marker according to claim 10, wherein the depth of the at least one cavity essentially corresponds to a thickness of the one or more optically detectable elements.

12. The marker according to claim 1, wherein the structure and/or at least one of the one or more supporting elements is/are spring-loaded and provide(s) a detachable positive fit and/or frictional fit between the structure and at least one of the one or more supporting elements and/or retain an optically detectable element supported by a supporting element.

13. The marker according to claim 1, wherein the structure and/or at least one of the one or more supporting elements comprise(s) a release section which is resiliently hinged to the structure and/or supporting element and configured to release the positive fit or frictional fit formed between the structure and the supporting element.

14. The marker according to claim 1, wherein at least one of the one or more supporting elements comprises a gripping section which protrudes from the first opening.

15. The marker according to claim 1, wherein a position of a plurality of the at least two second openings with respect to each other conforms to a predetermined marker arrangement which is recognised by an optical medical tracking system.

16. A marker for optical medical navigation, the marker comprising a structure with a recess, and a supporting element, wherein the supporting element is accommodated within the recesses and supports an optically detectable element wherein the recess has a first opening which allows the optically detectable element together with the supporting element to be introduced into the recess, and wherein:
the recess has at least two second openings which are different from the first opening, wherein the at least two second openings have a predetermined contour and allow the optically detectable element to be optically detected therethrough, wherein the structure and the supporting element retain the optically detectable element within the recess, and wherein a detectable shape of the optically detectable element is confined by the predetermined contour of the at least two second openings.

17. The marker according to claim 16, wherein the optically detectable element comprised a reflective layer.

18. The marker according to claim 16, wherein the structure and/or the supporting element comprises a release section which is resiliently hinged to the structure and/or supporting element and configured to release a positive fit or a frictional fit formed between the structure and the supporting element.

19. The marker according to claim 16, wherein the supporting element comprises a gripping section which protrudes from the first opening.

* * * * *

UNITED STATES PATENT AND TRADEMARK OFFICE
CERTIFICATE OF CORRECTION

PATENT NO. : 10,335,239 B2
APPLICATION NO. : 14/760747
DATED : July 2, 2019
INVENTOR(S) : Norman Plassky et al.

Page 1 of 1

It is certified that error appears in the above-identified patent and that said Letters Patent is hereby corrected as shown below:

In the Claims

Column 6, Line 23 of Claim 1, "mote" should be changed to "more"

Column 6, Line 31 of Claim 1, "the at least" should be changed to "at least"

Signed and Sealed this
Third Day of September, 2019

Andrei Iancu
*Director of the United States Patent and Trademark Office*